US010208318B2

(12) United States Patent
Barkats (10) Patent No.: US 10,208,318 B2
(45) Date of Patent: *Feb. 19, 2019

(54) CNS GENE DELIVERY USING PERIPHERAL ADMINISTRATION OF AAV VECTORS

(75) Inventor: Martine Barkats, Charenton-le-pont (FR)

(73) Assignees: GENETHON, Evry (FR); CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 12/452,789

(22) PCT Filed: Jul. 22, 2008

(86) PCT No.: PCT/EP2008/059595
§ 371 (c)(1),
(2), (4) Date: Jan. 22, 2010

(87) PCT Pub. No.: WO2009/013290
PCT Pub. Date: Jan. 29, 2009

(65) Prior Publication Data
US 2010/0130594 A1    May 27, 2010

(30) Foreign Application Priority Data

Jul. 23, 2007  (EP) .................................. 07301263

(51) Int. Cl.
*C12N 15/86* (2006.01)
*A61K 48/00* (2006.01)

(52) U.S. Cl.
CPC .......... *C12N 15/86* (2013.01); *A61K 48/0075* (2013.01); *C12N 2750/14143* (2013.01)

(58) Field of Classification Search
CPC ... C12N 15/86; C12N 15/861; A61K 48/0075
See application file for complete search history.

(56) References Cited

U.S. PATENT DOCUMENTS

| | | | |
|---|---|---|---|
| 7,465,583 B2 * | 12/2008 | Samulski et al. ............ | 435/456 |
| 2003/0118556 A1 * | 6/2003 | Kaspar et al. .............. | 424/93.2 |
| 2003/0161814 A1 * | 8/2003 | Wang et al. ................ | 424/93.2 |
| 2003/0219414 A1 * | 11/2003 | Podsakoff et al. .......... | 424/93.2 |
| 2004/0029106 A1 | 2/2004 | Samulski et al. | |
| 2005/0014262 A1 * | 1/2005 | Gao et al. .................... | 435/456 |
| 2005/0032219 A1 * | 2/2005 | Aubourg et al. ............ | 435/456 |
| 2006/0110364 A1 | 5/2006 | Harding | |
| 2007/0003524 A1 | 1/2007 | Kaspar | |
| 2007/0036760 A1 * | 2/2007 | Wilson et al. ............... | 424/93.2 |
| 2008/0188431 A1 * | 8/2008 | Chiorini ............... | C07K 14/005 514/44 R |
| 2009/0087413 A1 | 4/2009 | Shepard | |
| 2010/0129405 A1 | 5/2010 | Schmidt et al. | |
| 2010/0221225 A1 * | 9/2010 | Byrne et al. ................ | 424/93.2 |
| 2010/0240739 A1 | 9/2010 | Barkats | |
| 2010/0297084 A1 * | 11/2010 | Bennett et al. ............. | 424/93.2 |

FOREIGN PATENT DOCUMENTS

| | | | |
|---|---|---|---|
| EP | 2 019 143 | | 1/2009 |
| WO | 03/055983 | | 7/2003 |
| WO | WO/2005/033321 | * | 4/2005 |
| WO | WO 2005/056807 A2 | | 6/2005 |
| WO | 2005/084705 | | 9/2005 |

OTHER PUBLICATIONS

Inagaki et al Molecular Therapy, 2006, 14 (1), 45-53.*
Cearley et al Molecular Therapy (2006) 13, 528-537).*
Mingozzi et al (Nature Review, 2011, 341-355.*
Suzuki et al (Acta Pediatr. Suppl. 2003, 443, 54-62.*
Walkley et al , (Brain Pathol. 1998; 8(1):175-93.*
Schuchman EH, Chemistry and Physics of lipids 102: 179-188, 1999.*
Foust et al Nature Biotechnology, 2010, 271-276.*
Foust et al Nature Biotechnology, 2009, 27, 56-65.*
Picher-Martel et al Acta Neuropathologica Communications (2016) 4:70, 1-29.*
Wirth et al Expert opinion on Emerging Drug, 2015, 20, 3, 353-356.*
Passini et al Trends in Molecular Medicine, 2011, 17, 5, 259-264.*
Dayton et al Expert Opinion Biol Ther, 2012, 757-766.*
Cearley et al (Molecular Therapy, 2006, 13(3), 528-536.*
Broekman et al., "Complete Correction of Enzymatic Deficiency and Neurochemistry in the GM1-Gangliosidosis Mouse Brain by Neonatal Adeno-Associated Virus-Mediated Gene Delivery", www.moleculartherapy.org vol. 15, No. 1, pp. 30-37, Jan. 2007.
Mouri et al., "Oral Vaccination with a Viral Vector Containing a Beta cDNA Attenuates Age-Related a Beta Accumulation and Memory Deficits without Causing Inflammation in a Mouse Alzheimer Model", FASEB Journal, vol. 21, No. 9, Jul. 2007, pp. 2135-2148.
Passini et al., "Combination Brain and Systemic Injections of AAV Provide Maximal Functional and Survival Benefits in the Niemann-Pick Mouse", Proceedings of the National Academy of Sciences of the United States of America, vol. 104, No. 22, May 2007, pp. 9505-9510.
Carlsson et al., "Reversal of Dyskinesias in Animal Model of Parkinson's Disease by Continuous L-DOPA Delivery using rAAV Vectors", Brain (2005), No. 128, pp. 559-569.
Boulis et al., "Adeno-Associated Viral Vector Gene Expression in the Adult Rat Spinal Cord Following Remote Vector Delivery", Neurobiology Disease, Blackwell Scientific Publications, Oxford, GB, vol. 14, No. 3, Dec. 1, 2003, vol. 14, No. 3, pp. 535-541.
Fu et al., "Self Complementary Adeno-Associated Virus Serotype 2 Vector: Global Distribution and Broad Dispersion of AAV-Mediated Transgene Expression in mouse brain" Molecular Therapy, Academic Press, San Diego, CA, US, vol. 8, No. 6, Dec. 1, 2006, pp. 911-917.

(Continued)

*Primary Examiner* — Anoop K Singh
(74) *Attorney, Agent, or Firm* — Arrigo, Lee, Guttmann & Mouta-Bellum LLP (57) ABSTRACT

The present invention relates to compositions and methods for the delivery of therapeutic proteins to the CNS using recombinant AAV vectors. More specifically, the invention relates to compositions and methods for delivering proteins into the cerebrospinal fluid of mammalian subjects through peripheral administration of AAV vectors. The invention may be used to treat various disorders of the central nervous system, including degenerative diseases and motor neuron diseases.

11 Claims, 4 Drawing Sheets

(56) References Cited

OTHER PUBLICATIONS

Hollis et al., "Efficient Retrograde Neuronal Transduction Utilizing Self-Complementary AAV1," Molecular Therapy: The Journal of the American Society of Gene Therapy, vol. 16, No. 2, Feb. 2008, pp. 296-301.

Inagaki et al., "Robust Systemic Transduction with AAV9 Vectors in Mice: Efficient Global Cardiac Gene Transfer Superior to that of AAV8", Molecular Therapy, Academic Press, San Diego, CA, US, vol. 14, No. 1, Jul. 1, 2006, pp. 45-53.

Kaspar et al., "Retrograde Viral Delivery of IGF-1 Prolongs Survival in a Mouse ALS Model", Science, American Association for the Advancement of Science, US, Washington, DC, vol. 301, No. 5634, Aug. 8, 2003, pp. 839-842.

Pirozzi et al., Intramuscular Viral Delivery of Paraplegin Rescues Peripheral Axonopathy in a Model of Hereditary Spastic Paraplegia, Journal of Clinical Investigation, vol. 116, No. 1, Jan. 2006, pp. 202-208.

Azzouz et al, "Lentivector-mediated SMN replacement in a mouse model of spinal muscular atrophy", The Journal of Clinical Investigation, vol. 114, No. 12, Dec. 2004, pp. 1726-1731.

Cearley et al., "Transduction Characteristics of Adeno-associated Virus Vectors Expressing Cap Serotypes 7, 8, 9, and Rh10 in the Mouse Brain," Molecular Therapy, vol. 13, No. 3, pp. 528-537 (Mar. 2006).

Dominguez et al., "Intravenous scAAV9 delivery of a codon-optimized SMN1 sequence rescues SMA mice," Human Molecular Genetics, 2011, vol. 20, No. 4, pp. 681-693 (2011).

Duque et al., "Intravenous Administration of Self-complementary AAV9 Enables Transgene Delivery of Adjust Motor Neurons," Molecular Therapy, vol. 17, No. 7, pp. 1187-1196 (Jul. 2009).

Foust et al., "Intravascular AAV9 preferentially targets neonatal neurons and adult astrocytes," Nature Biotechnology—Advance Online Publication, 2008 Nature Publishing Group, pp. 1-7.

Foust et al., "Rescue of the spinal muscular atrophy phenotype in a mouse model by early postnatal delivery of SMN," Nature Biotechnology—Advance Online Publication, 2010 Nature America, Inc., pp. 1-6.

International Search Report for PCT/EP2008/059595, dated Nov. 6, 2008.

Loeb et al., "Enhanced Expression of Transgenes from Adeno-Associated Virus Vectors with the Woodchuck Hepatitis Virus Posttranscriptional Regulatory Element: Implications for Gene Therapy," Human Gene Therapy, vol. 10, pp. 2295-2305 (Sep. 20, 1999).

Lowenstein, "Crossing the Rubicon," Nature Biotechnology, vol. 27, No. 1, pp. 42-44 (Jan. 2009).

Mori et al., "Two novel adeno-associated viruses from cynomolgus monkey: pseudotyping characterization of capsid protein," Virology, vol. 330, pp. 375-383 (2004).

Rahim et al., "Intravenous administration of AAV2/9 to the fetal and neonatal mouse leads to differential targeting of CNS cell types and extensive transduction of the nervous system," The FASEB Journal, vol. 25, pp. 3505-2518 (Oct. 2011).

Written Opinion of the International Searching Authority for PCT/EP2008/059595, dated Nov. 6, 2008.

\* cited by examiner

Figure 5

CNS GENE DELIVERY USING PERIPHERAL ADMINISTRATION OF AAV VECTORS

This application is the U.S. national phase of International Application No. PCT/EP2008/059595, filed 22 Jul. 2008, which designated the U.S and claims priority to European Application No. 07301263.5, filed 23 Jul. 2007, the entire contents of each of which are hereby incorporated by reference.

The present invention relates to compositions and methods for the delivery of therapeutic proteins to the CNS using recombinant AAV vectors. More specifically, the invention relates to compositions and methods for delivering proteins into the cerebrospinal fluid of mammalian subjects through peripheral administration of AAV vectors. The invention may be used to treat various disorders of the central nervous system, including degenerative diseases and motor neuron diseases.

BACKGROUND

The long-term production of therapeutic proteins in the cerebral ventricles represents a recognized approach for neuroprotection in central nervous diseases. For example, intra-cerebroventricular (ICV) delivery of the VEGF (vascular endothelial growth factor) recombinant protein was reported to delay motor neuron degeneration in a rat model of amyotrophic lateral sclerosis (ALS) {Storkebaum, 2005 #22}. In this study, VEGF was delivered to the brain ventricles by stereotaxic implantation of a catheter linked to an osmotic minipump.

ICV injection of recombinant gene vectors is a convenient way to induce the continuous production of therapeutic proteins into the cerebrospinal fluid (CSF) through the transduction of the ependymal and choroids plexus cells {Broekman, 2007 #37}. This approach has been reported to be efficient for correction of the neuropathology in animal models of lysosomal diseases, by mediating gene delivery of lysosomal enzymes to the brain. For example, a recent study demonstrated that the direct neonatal ICV injection of an AAV expressing the lysosomal acid β-galactosidase was able to mediate the delivery of the enzyme to the brain and to restore normal levels of glycosphingo lipids {Broekman, 2007 #48}.

The delivery of proteins into the CSF thus represents an effective approach for the treatment of central nervous system (CNS) pathologies. However, the existing techniques to achieve such delivery require direct injection of gene vectors into the brain and/or surgery, and substantial risks related to the injection procedure (e.g., intracerebral surgery, infection or inflammation due to the blood brain barrier breaking, etc.), circumvent the clinical applications of this strategy.

WO2005/056807 relates to the identification of bovine AAV and proposes to use the same for gene delivery in vivo, including for treating CNS disorders. This application includes a discussion of the transcytosis property (i.e., active membrane transport) of AAV through the epithelium barrier. It is suggested the possibility of achieving CNS gene delivery either through ex vivo transplantation or injection of AAV-engineered cells, or through direct in vivo injection of the vectors.

However, the application is based on in vitro experiments showing Bovine AAV and AAV4 infection of bovine brain primary endothelia cells in culture.

SUMMARY OF THE INVENTION

The present invention relates to novel compositions and methods for the delivery of therapeutic proteins to the CNS using recombinant AAV vectors. More specifically, the invention relates to compositions and methods for delivering proteins into the cerebrospinal fluid of mammalian subjects through peripheral administration of AAV vectors.

An object of this invention more specifically relates to the use of an AAV vector encoding a therapeutic protein for the manufacture of a medicament for treating a CNS disorder in a subject, wherein said AAV vector is administered by peripheral injection to said subject, said injection allowing infection of cerebrospinal fluid secretory cells of the brain (e.g., the epithelial cells of the plexus choroids and/or the ependyma and/or a meningeal membrane) and subsequent secretion of the therapeutic protein into the cerebrospinal fluid.

A further object of this invention resides in the use of an AAV vector encoding a therapeutic protein for the manufacture of a medicament for treating a CNS disorder through secretion of said therapeutic protein into the cerebrospinal fluid following peripheral injection of said vector.

Another object of this invention relates to the use of an AAV vector for the manufacture of a medicament for secreting a protein into the cerebrospinal fluid of a subject by peripheral injection of said vector under conditions allowing infection of cerebrospinal fluid secretory cells of the brain (e.g., the epithelial cells of the plexus choroids and/or the ependyma and/or a meningeal membrane).

The invention also relates to the use of an AAV vector for the manufacture of a medicament for expressing a recombinant protein into cerebrospinal fluid secretory cells of the brain (e.g., the epithelial cells of the plexus choroids and/or of the ependyma and/or a meningeal membrane) of a subject, wherein said vector is administered to the subject by peripheral injection.

Still a further object of this invention is a method of delivering a protein to the cerebrospinal fluid of a subject, the method comprising peripherally administering to said subject an AAV vector encoding said protein, said peripheral administration allowing infection of cerebrospinal fluid secretory cells of the brain (e.g., the epithelial cells of the plexus choroids and/or of the ependyma and/or a meningeal membrane) in said subject and secretion of said protein into the cerebrospinal fluid.

A further object of this invention is a method of infecting cerebrospinal fluid secretory cells of the brain (e.g., the epithelial cells of the plexus choroids and/or of the ependyma and/or a meningeal membrane) of a subject, comprising peripherally administering to the subject an amount of an AAV vector effective at infecting such cells.

A further object of this invention is a method of treating a CNS disorder in a subject by delivering a therapeutic protein into the cerebrospinal fluid of said subject, the method comprising peripherally administering to the subject an amount of an AAV vector encoding said protein effective to allow infection of cerebrospinal fluid secretory cells of the brain (e.g., the epithelial cells of the plexus choroids and/or of the ependyma and/or a meningeal membrane) by said AAV vectors in the subject, said infection causing expression of the encoded therapeutic protein into the cerebrospinal fluid and treating said disorder.

A further object of this invention is an improvement to methods of treating a CNS disorder in a subject by delivery of a therapeutic protein into the cerebrospinal fluid of said subject, the improvement comprising delivering said therapeutic protein through peripheral administration to the subject of an AAV vector in an amount effective to cause infection of cerebrospinal fluid secretory cells of the brain (e.g., the epithelial cells of the plexus choroids and/or of the ependyma and/or a meningeal membrane).

As will be disclosed in the present application, this invention represents a safe and convenient means to deliver therapeutic proteins to the CNS through their secretion into the CSF. The invention is suitable for delivering any therapeutic protein, in any mammalian subject, including human subjects, for treating various CNS conditions.

LEGEND TO THE FIGURES

FIG. 1. Widespread gene delivery to the central nervous system (CNS) and muscles of neonatal mice after intramuscular injection with different serotypes and genomes of AAV vectors. Representative sections showing mSEAP histochemical staining from each group (n=3 mice/group) (A) Cross-sections of the AAV-injected gastrocnemius muscles (B) Magnified views of the choroids plexus in the third ventricule of AAV-injected mice and a non-injected control (C) Magnified view of blood vessels in the brain and the spinal cord of scAAV9-injected mice. PN4, post-natal 4; PN8, post-natal 8; ss, single-strand; sc: self-complementary. (D) Comparison of transduction efficiency in the brain of i.p. AAV-injected mice (3.10e9 vg). Illustrative brain sections from mice i.p. injected with the 4 AAV vectors. Sections were treated for mSEAP histochemistry. A very intense mSEAP expression was detected in the choroid plexus of scAAV9 injected mice. A near similar mSEAP activity was detected in the choiroid plexus from ssAAV1-, scAAV1, and ssAAV9-injected mice.

FIG. 3. GFP expression in the CNS of neonatal mice seven days after intraperitoneal injection of scAA9-GFP. Representative photomicrographs of brain and spinal cord histological sections showing GFP immunostaining. Transgene expression was detected in (A, B) the choroids plexus, (A, C) the hippocampus (arrow and arrowhead indicate cells with glial and neuronal morphology, respectively), (D) the entorhinal cortex (arrows indicate cells with a typical neuronal morphology) and (E) the corticospinal tract (at the level of the pyramidal decussation in the cervical spinal cord).

FIG. 4. Representative photomicrographs of GFP expression in the CNS of neonatal mice after intramuscular injection of GFP-scAAV9 expressing vectors. Brain and spinal cord histological sections were treated with GFP immunostaining seven days post-injection. Transgene expression was detected in (A) the epithelial cells of the choroids plexus (arrow) and the ependyma (arrowheads) (B) neuronal cells in the septum (arrows) and (C) corticospinal tract fibers in the spinal cord (arrows).

FIG. 5. GFP expression in the CNS of neonatal mice seven days after intravenous injection of scAAV9 vectors. Representative photomicrographs of brain histological sections treated for GFP immunostaining GFP-positive cells were detected in (A) the epithelial cells of the choroids plexus (arrow) and the ependyma (arrowheads), (B) neuronal cells of the entorhinal cortex, (C, D) neuron-like and glial-like cells of the hippocampus

DETAILED DESCRIPTION OF THE INVENTION

We describe herein a new gene transfer procedure for the delivery of therapeutic proteins into the CNS through peripheral injection of AAV gene vectors. This method is based on transgene delivery to cerebrospinal fluid secretory cells of the brain (i.e., cell populations or types which, within the brain, allow secretion of a product into the cerebrospinal fluid, such as the epithelial cells of the plexus choroids and/or of the ependyma and/or a meningeal membrane) through peripheral delivery of recombinant AAV gene vectors, allowing secretion of encoded therapeutic proteins into the CSF.

Figure 1:
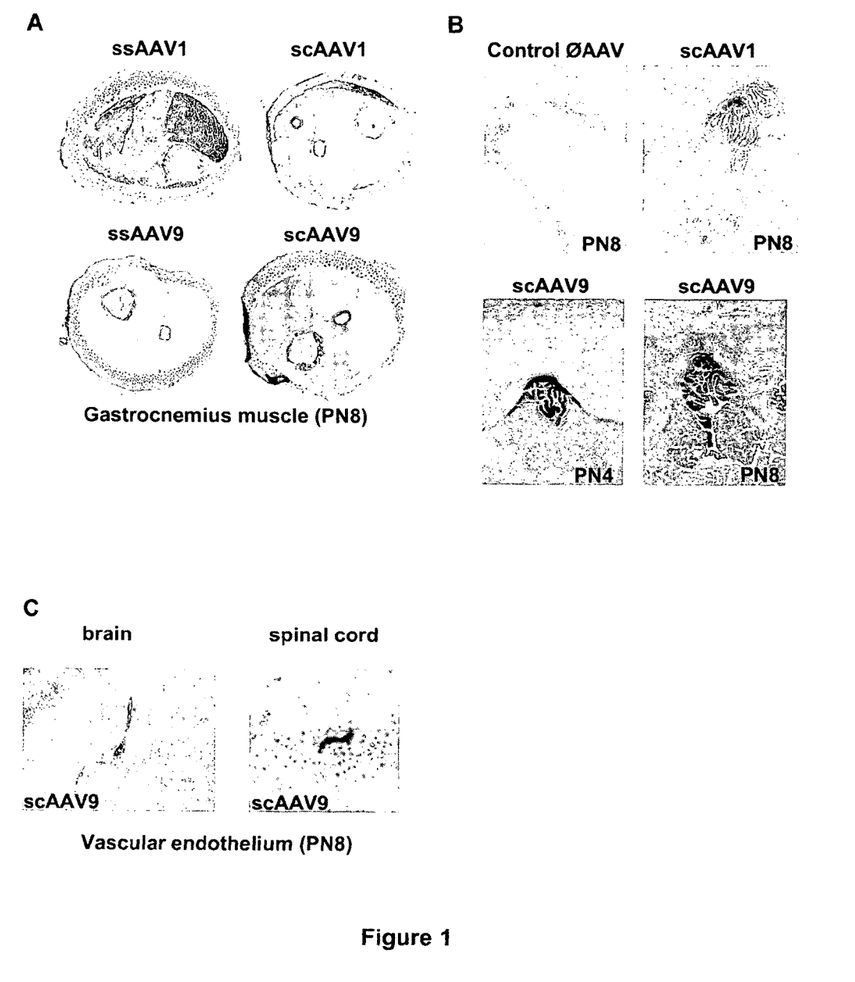

As disclosed in the examples, the distribution of transgene expression after peripheral administration (e.g., i.m., i.p, or i.v. injections) of recombinant single stranded (ss) or double-stranded self-complementary (sc) AAV vectors in neonatal and adult C57Bl/6 mice was analyzed. These vectors expressed either the murine secreted alkaline phosphatase (SEAP) or the green fluorescent protein (GFP), under control of the CMV promoter. The results presented in the experimental section surprisingly show that, after peripheral injection(s) of either conventional or self-complementary AAV9-GFP in neonatal mice, a high transgene expression level is detected in the choroids plexus and ependyma cells as well as in meningeal membranes. The transduction efficiency was found to be increased after peripheral injection in the adult mouse of highly concentrated stocks of scAAV9. After systemic delivery of both mSEAP-expressing AAV9 and AAV1 in adult mice, a significant increase of mSEAP activity was found in the CNS tissue samples. Expression of mSEAP was also detected in the choroid plexus of ssAAV9 and AAV1 (ss and sc) injected mice, as seen on brain sections treated for mSEAP histochemistry (FIG. 1D).

Such a peripheral delivery of recombinant AAV vectors allows the targeting and the long-term secretion of therapeutic proteins into the CSF. The i.v. injection of a scAAV9 encoding the vascular endothelial growth factor (VEGF) in neonatal mice allowed the production of the secreted protein in the CNS up to 5 months following injection (the last time that was examined). This gene transfer strategy represents therefore an efficient and non-invasive procedure to reach the CNS, which allows avoiding the risks linked to the surgery procedure and by-passing the problem of the blood brain barrier. The present invention thus has many implications and utilities in the treatment of CNS disorders, including neurodegenerative diseases and motor neuron diseases.

AAV Vectors

Within the context of the present invention, the term "AAV vector" designates any vector which comprises or derives from components of AAV and is suitable to infect mammalian cells, preferably human cells. The term AAV vector typically designates an AAV type viral particle (or virion) comprising at least a nucleic acid molecule encoding a therapeutic protein. As will be discussed below, the AAV may be derived from various serotypes, including combinations of serotypes (i.e., "pseudotyped" AAV) or from various genomes (e.g. single-stranded or self-complementary). In addition, the AAV vector may be replication defective and/or targeted.

Adeno-associated virus (AAV) is a dependent parvovirus, of approximately twenty nanometers in size. Like other parvoviruses, AAV is a single-stranded, non-enveloped DNA virus, having a genome of about 5000 nucleotides in length, containing two open reading frames. The left-hand open reading frame codes for the proteins responsible for replication (Rep), while the right-hand open reading frame encodes the structural proteins of the capsid (Cap). The open reading frames are flanked by two ITR sequences, which serve as the origin of replication of the viral genome. Furthermore, the genome also contains a packaging sequence, allowing packaging of the viral genome into an AAV capsid.

AAV requires co-helper functions (which may be provided e.g. by an adenovirus, or by suitable packaging cells or helper plasmids) to undergo a productive infection in cultured cells. In the absence of such helper functions, the AAV virions essentially enter the cells, migrate to the nucleus as a single-stranded DNA molecule, and integrate into the cells' genome. AAV has a broad host range for infectivity, including human cells, is ubiquitous in humans, and is completely non-pathogenic.

AAV vectors have been designed, produced and used to mediate gene delivery in human subjects, including for therapeutic purposes. Clinical trials are presently ongoing in various countries using AAV vectors. Typically, AAV vectors for use in gene transfer comprise a replication defective AAV genome lacking functional Rep and Cap coding viral sequences. Such replication defective AAV vectors more preferably lack most or all of the Rep and Cap coding sequences, and essentially retain one or two AAV ITR sequences and a packaging sequence.

Methods of producing such AAV vectors have been disclosed in the literature, including using packaging cells, auxiliary viruses or plasmids, and/or baculovirus systems (Samulski et al., (1989) J. Virology 63, 3822; Xiao et al., (1998) J. Virology 72, 2224; Inoue et al., (1998) J. Virol. 72, 7024; WO98/22607; WO2005/072364). Methods of producing pseudotyped AAV vectors have also been reported (e.g., WO00/28004), as well as various modifications or formulations of AAV vectors, to reduce their immunogenicity upon in vivo administration (see e.g., WO01/23001; WO00/73316; WO04/112727; WO05/005610; WO99/06562).

AAV vectors may be prepared or derived from various serotypes of AAVs, which may be even mixed together or with other types of viruses to produce chimeric (e.g. pseudotyped) AAV viruses.

In a particular embodiment, the AAV vector for use in the present invention is a human serotype AAV vector. Such a human AAV may be derived from any known serotype, e.g. from any one of serotypes 1-11, more preferably from AAV1, AAV2, AAV4, AAV6 and AAV9. Specific examples of such AAV vectors are vectors comprising an AAV1-derived genome (a nucleic acid molecule comprising an AAV1-derived ITR and an AAV1-derived packaging sequence, operatively linked to a nucleic acid encoding a therapeutic protein, preferably two AAV1-derived ITR flanking an AAV1-derived packaging sequence and a nucleic acid encoding a therapeutic protein) in an AAV1-derived capsid; vectors comprising and AAV2-derived genome in an AAV2-derived capsid; vectors comprising and AAV4-derived genome in an AAV4-derived capsid; vectors comprising and AAV6-derived genome in an AAV6-derived capsid or vectors comprising and AAV9-derived genome in an AAV9-derived capsid In another particular embodiment, the AAV vector is a pseudotyped AAV vector, i.e. comprises sequences or components originating from at least two distinct AAV serotypes. In a particular embodiment, the pseudotyped AAV vector comprises an AAV genome derived from one AAV serotype, and a Capsid derived at least in part from a distinct AAV serotype. Specific examples of such pseudotyped AAV vectors include, without limitation, vectors comprising an AAV2-derived genome in an AAV1-derived capsid; or vectors comprising an AAV2-derived genome in an AAV6-derived capsid; or vectors comprising an AAV2-derived genome in an AAV4-derived capsid or vectors comprising an AAV2-derived genome in an AAV9-derived capsid.

In a further particular embodiment, which may be combined with any of the above embodiments, the AAV vector may comprise a modified capsid, including proteins or peptides of non viral origin or structurally modified, to alter the tropism of the vector. As a particular example, the capsid may include a ligand of a particular receptor, or a receptor of a particular ligand, to target the vector towards cell type(s) expressing said receptor or ligand, respectively.

In the AAV vectors used in the present invention, the AAV genome may be either a single stranded nucleic acid or a double stranded, self complementary nucleic acid (McCarty et al., Gene Therapy, 2001).

As discussed above, the AAV-derived genome comprises a nucleic acid encoding a therapeutic protein. Typically, the nucleic acid also comprises regulatory sequences allowing expression and, preferably, secretion of the encoded protein, such as e.g., a promoter, enhancer, polyadenylation signal, internal ribosome entry sites (IRES), sequences encoding protein transduction domains (PTD), and the like. In this regard, the nucleic acid most preferably comprises a promoter region, operably linked to the coding sequence, to cause or improve expression of the therapeutic protein in infected cells. Such a promoter may be ubiquitous, tissue-specific, strong, weak, regulated, chimeric, etc., to allow efficient and suitable production of the protein in the infected tissue. The promoter may be homologous to the encoded protein, or heterologous, including cellular, viral, fungal, plant or synthetic promoters. Most preferred promoters for use in the present invention shall be functional in human cells, particularly in human epithelial cells, most preferably in the plexus choroids or ependyma cells. Examples of such regulated promoters include, without limitation, Tet on/off element-containing promoters, rapamycin-inducible promoters and metallothionein promoters. Examples of promoters specific for the epithelial cells of the choroid plexus or ependyma cells include that of the aquaporin 1 (AQP1) or the HNF-3/fork head homolog-4 (HFH-4) or the insulin-like growth factor II. Examples of ubiquitous promoters include viral promoters, particularly the CMV promoter, the RSV promoter, the SV40 promoter, etc. and cellular promoters such as the PGK (phosphoglycerate kinase) promoter.

In a preferred embodiment, the nucleic acid comprises a leader sequence allowing secretion of the encoded protein. Fusion of the transgene of interest with a sequence encoding a secretion signal peptide (usually located at the N-terminal of secreted polypeptides) will allow the production of the therapeutic protein in a form that can be secreted from the transduced cell into the CSF. Examples of such signal peptides include the albumin, the β-glucuronidase, the alkaline protease or the fibronectin secretory signal peptides.

According to another specific embodiment, the transgene is fused with PTD sequences, such as the Tat or VP22 sequences, in order to cause or improve secretion of the therapeutic protein from the transduced cells and re-uptake by neighbour ones.

In a particular embodiment the nucleic acid comprises, operably linker, a promoter and a leader sequence, to allow expression and secretion of the encoded protein.

In a further particular embodiment, the nucleic acid comprises, operably linker, a promoter, a leader sequence and a PTD sequence, to allow expression and secretion of the encoded protein.

In a most preferred embodiment, the promoter is specific for the epithelial cells of the choroids plexus or the ependyma, i.e., allows preferential expression of the transgene in said cells.

As discussed above, the AAV vectors may be produced by techniques known per se in the art, as further illustrated in the examples.

Peripheral Administration

The invention is based on the demonstration that effective and long term expression of proteins into the CSF can be achieved with non-invasive techniques, through peripheral administration of AAV vectors. Such peripheral administration includes, without limitation, any administration route which does not imply direct injection into the brain. More particularly, peripheral administration comprises systemic injections, such as intramuscular (i.m.), intravenous (i.v.), intraperitoneal (i.p.), intra-arterial, sub-cutaneous or transdermic injections. Peripheral administration also includes oral administration of AAV vectors (WO96/40954), delivery using implants (WO 01/91803), or administration by instillation through the respiratory system, e.g., using sprays, aerosols or any other appropriate formulations.

Most preferred peripheral administration includes peripheral injection, in particular systemic injection, most preferably i.m., i.p. or i.v. injection.

The doses of AAV vectors may be easily adapted by the skilled artisan, e.g., depending on the disease condition, the subject, the treatment schedule, etc. Typically, from $10^5$ to $10^{14}$ viral genomes (transducing units) are administered per dose, typically from $10^5$ to $10^{12}$, from $10^6$ to $10^{11}$, from $10^7$ to $10^{11}$, from $10^8$ to $10^{11}$. Exemplary doses for achieving therapeutic effects are virus titers of at least about $10^5$, $10^6$, $10^7$, $10^8$, $10^9$, $10^{10}$ or $10^{11}$ transducing units or more, preferably between about $10^{10}$ and $10^{13}$. A preferred effective dose within the context of this invention is a dose allowing infection of cells of the plexus choroids or ependyma.

The AAV vector may be administered in any suitable form, either as a liquid solution or suspension, as a solid form suitable for solution or suspension in liquid prior to injection, as a gel or as an emulsion. The AAV vectors are typically formulated with any appropriate and pharmaceutically acceptable excipient, carrier, adjuvant, diluent, etc. For injection, the excipient may be a liquid, isotonic solution, buffer, such as a sterile and pyrogen-free water or a sterile and pyrogen-free phosphate-buffered saline solution. For inhalation, the excipient may be in particulate form.

The AAV vectors are typically administered in a "therapeutically-effective" amount, i.e., an amount that is sufficient to alleviate (e.g., decrease, reduce) at least one of the symptoms associated with the disease state, or to provide improvement in the condition of the subject. It should be pointed out that repeated administrations may be performed, if required, using either the same or different peripheral administration route and/or the same or distinct AAV serotypes.

CNS Disorder

The invention may be used to treat a variety of disorders through delivery of a therapeutic product into the CSF. The therapeutic product may be any protein, peptide or RNA that may alleviate or reduce symptoms that result from an absence or defect in a protein in a cell or subject or that otherwise confers a benefit to a subject. Examples of therapeutic proteins include growth factors, cytokines, hormones, neurotransmitters, enzymes, anti-apoptotic factors, angiogenic factors, and any protein known to be mutated in pathological disorders such as the "survival of motor neuron" protein (SMN).

Depending on the therapeutic product, the invention can be used to treat various diseases, including any disease which may be treated or prevented by expressing therapeutic proteins into nervous tissue. Such diseases include CNS disorders, preferably selected from neurodegenerative diseases, neuromuscular diseases, lysosomal diseases, trauma, bone marrow injuries, cancers of the nervous system, demyelinating diseases, autoimmune diseases of the nervous system, neurotoxic syndromes, sleeping disorders.

Specific examples of diseases include Alzheimer's Disease, Parkinson's Disease, Huntington's Disease, Tourette Syndrome, schizophrenia, Sly disease, Hunter's disease, dementia, paranoia, obsessive compulsive disorder, learning disabilities, ALS, spinal muscular atrophy, Charcot-Marie Tooth disease, Kennedy's disease, glioblastoma, neuroblastoma, autism, Gaucher's disease, Hurler's disease, Krabbe's disease and altered behaviors (e.g., disorders in sleeping, perception or cognition).

The invention may be used in any mammalian, particularly in human subjects, including adults, for preventive or curative treatment.

Further aspects and advantages of the present inventions will be disclosed in the following experimental section, which shall be considered as illustrative only, and not limiting the scope of this application.

EXAMPLES

1. Materials and Methods 1.1. Production of the Recombinant AAV Vectors {Riviere, 2006 #39}

The serotype 1 and 9 conventional single-stranded (ss) and self-complementary double-stranded (sc) ssAAV vectors were generated by packaging AAV2 genomes in AAV1 and 9 capsids. Briefly, the vectors were produced using a helper-virus free three-plasmid transfection with (1) the adenovirus helper plasmid (2) the AAV packaging plasmid encoding the rep and cap genes (3) the AAV2 vector plasmid containing mSEAP or GFP (under control of the cytomegalovirus promoter) as ss or sc genome. This latter plasmid was constructed by deleting the "D" and terminal resolution site (TRS) sequences at the 5' end of the genome {Veron, 2007 #40}.

The recombinant vectors were purified by double-CsCl ultracentrifugation followed by dialysis against phosphate buffer saline. Physical particles were quantified by Taqman and the vectors titers were expressed as viral genome (vg) per ml.

1.2. Animals.

Pregnant C57Bl/6 mice were purchased from Charles River Laboratories (Les Oncins, France) and neonates were injected on the day of birth (PN1). All animal experiments were carried out according to the European guidelines for the human care and use of experimental animals.

1.3. In Vivo Injections of the AAV Vectors

—Intramuscular Injections:

AAV vector solutions (ssAAV1 (n=2), ssAAV9 (n=2), scAAV1 (n=2) or scAAV9 (n=3) encoding mSEAP or GFP were injected into both triceps and gastrocnemius muscles in one day old C57B16 mice (1 injection site per muscle, 5 microliters per injection, $8.10^{+9}$ to $2.10^{+10}$ viral genome per mouse).

—Intraperitoneal Injections:

The viral solutions (ssAAV1, n=2, ssAAV9, n=1, scAAV1, n=1 and scAAV9, n=2) encoding mSEAP or GFP were injected into the peritoneal cavity of one day old C57B16 mice (100 µl, $3.10^{+10}$ to $10^{+11}$ viral genome per mouse).

—Intraveinous Injections:

The viral solutions (scAAV9-GFP, n=3) were injected into the temporal vein of one day old C57B16 mice (50 µl, 1, $5.10^{+10}$ viral genome per mouse).

1.4. Evaluation of Transgene Expression mSEAP Histochemistry:

Muscles, brains and spinal cords were removed at one (PN2), three (PN4) or seven (PN8) days post-injection, frozen in cold isopentane (−50° C.), and maintained at −80° C. for extemporal use.

Tissue sections of 16 µm thick for brain and spinal cord, and 8 µm thick for muscles were performed in a cryostat and subsequently processed for transgene expression. The sections were washed with PBS and endogenous alkaline phosphatase was heat-inactivated for 30 min at 65° C. Sections were then incubated overnight at 37° C. in 0.165 mg/ml 5-bromo-4-chloro-3-indolylphosphate and 0.33 mg/ml of nitroblue tetrazolium in 100 mM Tris-HCl, 100 mM NaCl and 50 mM MgCl2, counterstained with hematoxylin-eosin, and mounted with Eukit.

GFP Immunohistochemistry:

Muscles, brains and spinal cords were removed at one, three or seven days post-injection and fixed for 4 h with 4% paraformaldehyde in PBS. Tissues were then cryoprotected overnight at 4° C. in 15% sucrose for brains and muscles, and 30% sucrose for spinal cord and then frozen in cold isopentane (−50° C.). Serial sections were cut on a cryostat and stored at −80° C. for further analysis.

Sections were washed in PBS and incubated for 30 min in a solution of hydrogen peroxide (Peroxydase-Blocking solution, Dako) for inhibition of the endogenous peroxidases. After washing in PBS, sections were blocked for one hour at room temperature in PBS with 10% goat serum (Dako) and 0.4% Triton and then incubated overnight with a rabbit polyclonal anti-GFP (Abcam; 1/3000). A biotin-conjugated secondary antibody (Vectastain, 1:200) and the Vectastain Elite ABC kit were used, and DAB staining was revealed with the DAB substrate kit for peroxydase from Vector Laboratories. Sections were dehydrated in alcohol and xylen, and mounted with Eukit.

1.5. mSEAP Quantification Assay

Frozen tissues were lysed in 700 µl of nuclei lysis Buffer included in the Wizard genomic DNA extraction kit (Promega corporation, Madison, Wis.) containing a cocktail of protease inhibitor (Sigma-Aldrich, St. Louis, Mo.). The tissues were first homogenized for 30 sec with an Ultra-Turrax and then submitted to three successive homogenizations to achieve complete lysis. Cells membranes and debris were pelleted by centrifugation 2 minutes at 10,000 g at 4° C. mSEAP activity was measured in the supernatant using a chemiluminescent assay. Briefly, endogenous alkaline phosphates was heat inactivated 5 min at 65° C. and the heat resistant mSEAP was measured by addition of the reaction buffer and CPSD chemiluminescent substrate, according to the manufacturer's instructions (Tropix, Applied Biosystems, Forster City, USA). Chemiluminescence was quantified using a luminometer (Perkin Elmer, Walthan, Mass., USA). Expression levels are expressed as ng of mSEAP per lysate according to a standard curve of purified human placental alkaline phosphatase and are standardized per µg of protein using a nano-orange protein quantitation Assay® (Invitrogen, Carlsbad, Calif., USA).

1.6. VEGF ELISA Analysis

Quantitative analysis of VEGF levels was performed using a mouse VEGF immunoassay kit (Quantikine, R&D systems). 5 months after scAAV9-VEGF injection, the animals were deeply anaesthetized with pentobarbital and sacrificed by decapitation. Tissues samples were removed and frozen at −80° C. Tissues were homogenized in TSAI buffer (50 mM Tris-HCl, 250 mM NaCl, 5 mM EDTA, 0.1% NP40, 5 mM DTT, 10 mM NaF) containing a cocktail of protease inhibitor (Complete mini, Roche) using a motor pellet pestle for brain and spinal cord, and an Ultra-Turrax for heart and liver. The lysates were then centrifuged 20 min at 4° C., supernatants were collected and ELISA was performed following the manufacturer's protocol. Protein concentration was assessed using the BCA protein assay kit (Pierce).

2. Intramuscular Injections of mSEAP Expressing AAV

The ssAAV1, ssAAV9, scAAV1, or scAAV9 encoding mSEAP were injected into both triceps and gastrocnemius muscles in one day old C57B16 mice ($8.10^{+9}$ to $2.10^{+10}$ viral genome per mouse). The injected muscles, brains and spinal cords were removed one, three or seven days post injection, and mSEAP expression was determined using histochemistry (see materials and methods).

Expression of mSEAP was detected in the muscles from 3 days after injection of each AAV serotypes either conventional or self-complementary (except with ssAAV9), the expressing level dramatically increasing with time (FIG. 1A).

Transgene expression was also detected in the CNS after i.m. injection of scAAV9, and interestingly, the expression was specifically detected in the choroids plexus and ependymal cells (FIG. 1B), which are highly specialized epithelium in the secretion and the clearance of many proteins and toxins in the CSF {Redzic, 2005 #38}. The mSEAP expression in the CNS was found as soon as 3 days post-injection when using scAAV9, and the expression levels again increased with time. A weak expression was found with AAV1sc, but could be due to non-specific staining of the endogenous mSEAP.

A weak transgene expression was also detected in the spinal cord after i.m. injection of the scAAV9 vector. In this case, the mSEAP staining was almost visible in and around blood vessels of the spinal parenchyma (FIG. 1C).

Figure 2:
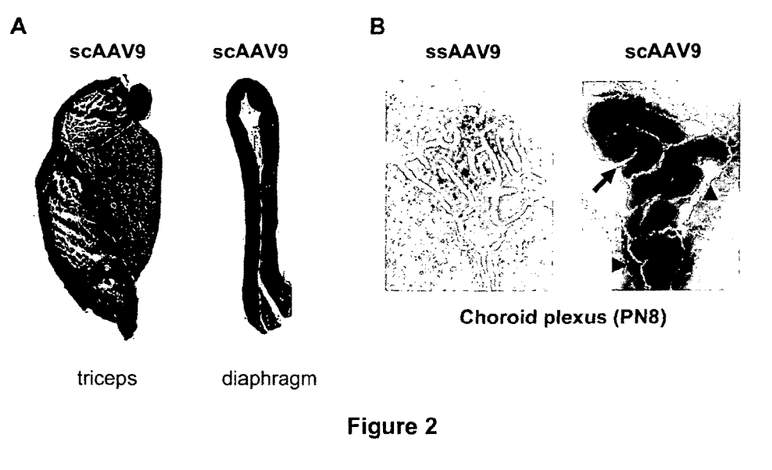
FIG. 2. Widespread gene delivery to the CNS and muscles of neonatal mice after intraperitoneal injection with sc- and ssAAV9 vectors. Representative sections showing mSEAP histochemical staining in (A) muscles, and (B) choroids. Arrow and arrowheads show transduced epithelial cells of the choroids and of the ependyma, respectively, in the AAV-injected mouse.

3—Intraperitoneal Injections of mSEAP Expressing AAV ssAAV1, ssAAV9, scAAV1 and scAAV9 were injected intraperitoneally in one day old C57B16 mice (100 µl, $3.10^{+10}$ to $1.10^{+11}$ viral genome per mouse) and transgene expression was evaluated in muscle or CNS tissue at 1, 3 or 7 days post injection. An mSEAP expression was found both in the muscle fibers and in the choroids plexus and ependyma cells as early as 3 days after injection of scAAV9, which considerably increased at 7 days post-injection (FIG. 2). Transgene expression was also observed within the blood vessels, both in the brain and throughout the spinal cord.

4—Transgene Expression in the CNS after Peripheral Injection of AAV-GFP

To determine whether mSEAP expression observed in the choroids plexus (after i.p. and i.m. injection of recombinant scAAV9) resulted from protein diffusion or from transgene expression within the choroids plexus cells, we analysed the expression pattern of the green fluorescent protein (GFP), a non-secreted protein, 7 days after peripheral injection of the corresponding AAV vector in neonatal mice.

Figure 3:
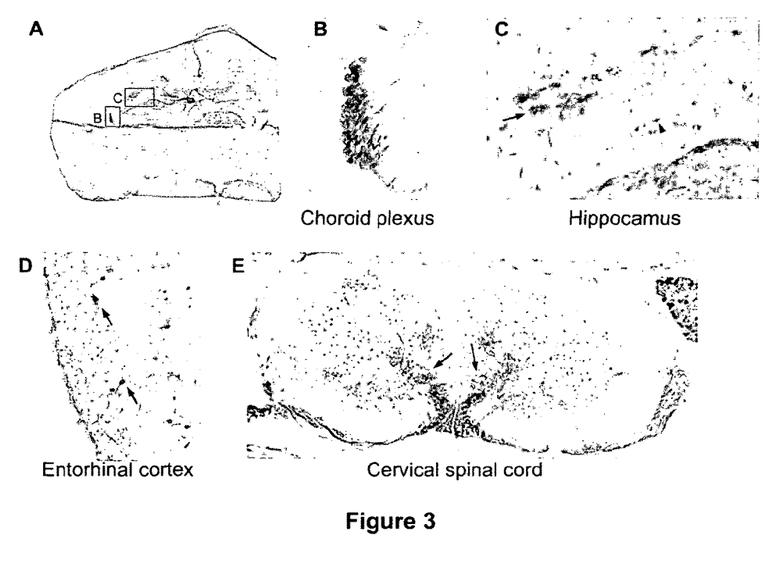
Figure 4:
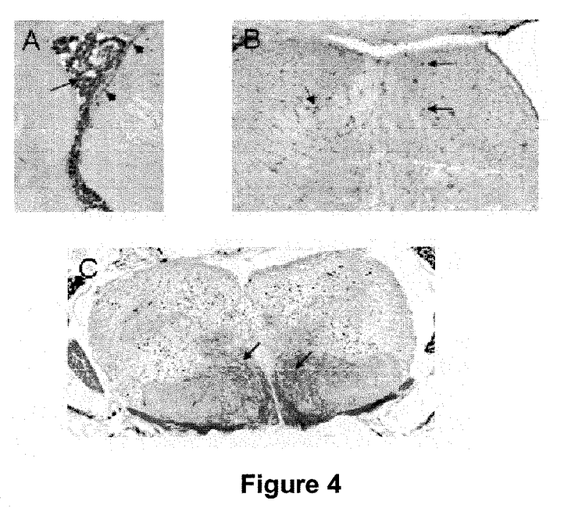

After i.p. (100 µl, $3.10^{+10}$ vg) and i.m. (5 µl per muscle, $8.10^{+9}$ vg) injection of scAAV9-GFP, GFP-immunoreactive cells were observed in both the choroids plexus and ependyma cells (FIGS. 3A,B and FIG. 4A). Importantly, we observed a strong GFP expression in many brain cells located for example in the hippocampus (FIGS. 3A, C), in the entorhinal cortex (FIG. 3D) or in the septum (FIG. 4B). A higher number of GFP-immunopositive cells were observed after i.p. than i.m. injection, but this could be due to the higher titre of vector used in the i.p. procedure. Additional data are required to confirm this observation.

A particularly high GFP-expression was found in the hippocampus, likely due to its location close to the cerebral ventricles and to the preferential diffusion of the vectors through the blood brain barrier at the choroids plexus level. Interestingly, highly transduced neuronal cells were also observed in the enthorhinal cortex, probably resulting from the retrograde axonal transport of the AAV vectors from the hippocampus. The presence of transduced neuronal cell in the septum could also result from similar axonal transport mechanisms.

GFP expression was further detected in blood vessels throughout the brain and the spinal cord.

Many GFP-positive fibers were also observed in the spinal grey matter innervating neuronal cells (that were identified using GFP/NeuN immunostaining) These fibers probably originate from the dorsal root ganglion which also appeared strongly positive (FIGS. 3E and 4C).

5—Intravenous Injections of GFP-Expressing AAV in Neonate Mice

A scAAV9 vector expressing GFP was injected intravenously into the temporal vein of one day old C57B16 mice (50 μl, 1, $5.10^{+10}$ viral genome per mouse) and transgene expression was analysed 7 days post-injection using immunohistochemistry against GFP.

Figure 5:
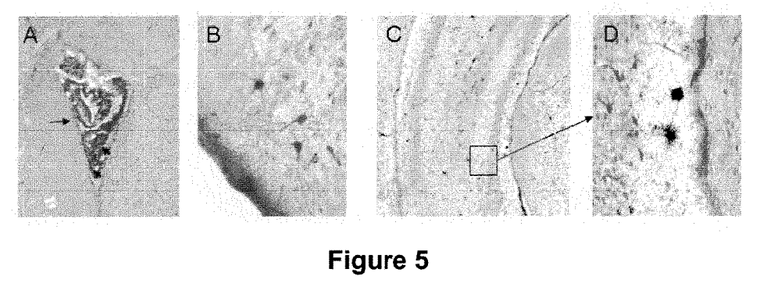

The immunohistochemical analysis of brain tissue sections revealed a strong GFP expression in both the choroids plexus and ependyma cells (FIG. 5A), and in the brain blood vessels Again, we found GFP expression within brain cells, with both a neuron-like and a glial-like phenotype, located for example in the hippocampus or in the entorhinal cortex (FIG. 5B-D).

Similar results were obtained when ssAAV9-GFP vectors were intravenously injected in neonatal mice aged of one day. In this case, the expression analysis was performed at 3 weeks after the AAV injections, which is the time necessary for the genome conversion into double-stranded DNA.

6—mSEAP Activity in Tissues from i.v.AAV-Injected Adult Mice

BBB formation is incomplete in neonatal mice. We therefore investigated whether CNS gene transfer in newborn mice was preserved in adults. Different serotypes (AAV1 and AAV9) of mSEAP-expressing AAV were injected into the tail vein of adult mice with increased doses of vector (3×1011 to 2×1012 vg in 500 μl per mouse) and the 1×1012 vg dose of scAAV9-mSEAP resulted in the efficient transduction of brain vessels and choroid plexus epithelial cells. Cell transduction efficiency was again higher for double-stranded (sc) than for conventional ssAA V9 vectors. To confirm the efficiency of this method for systemic gene transfer in the adult mouse CNS, ss- and sc AAV1 and AAV9 vectors encoding mSEAP were injected into the tail vein of adult mice (3×1011 or 1×1012 vg per mouse) and mSEAP activity was analyzed 4 weeks later by biochemical analysis. There was a large trend for a superior systemic gene delivery in all tissues from mice i.v. injected with scAA V9 vector (including non-nervous organs like the heart, skeletal muscle, liver and kidney) although mSEAP activity was also found to be increased in the CNS from was observed between mice AAV1-injected mice. Compared to the other serotypes, a 4- to 9-fold increase in the mean mSEAP activity was found in the brain, and a 2- to 17-fold increase in the spinal cord. mSEAP activity was also found up to 33-fold, 70-fold, 9-fold and 7-fold higher in the heart, triceps, liver, and kidney of animals injected with scAAV9 in comparison to those injected with the other vectors. Unexpectedly, mSEAP activity was higher in the spinal cord of ssAA V1—injected mice compared to ssAA V9 injected mice (and possibly in that of scAA V1—injected mice although not statistically significant).

Taken together, these results demonstrated that i.v. delivery of scAAV9 vectors can mediate gene transfer in the CNS of adult mice, in which the BBB is completely formed. This suggests the efficacy of the peripheral delivery of AAV9 and AAV1 to mediate production of a therapeutic protein in the CNS.

7—Long Term Expression of AAV-Mediated Delivery of VEGF in the CNS

In addition to the delivery of reporter transgenes, we also tested the efficiency and duration of scAAV9—mediated systemic transfer of a therapeutic gene, the vascular endothelial growth factor (VEGF). Several studies aiming at delivering VEGF to the MNs showed effectively an improvement of the ALS phenotype in animal models 15, 19. One day-old mice were injected into the temporal vein with 5×109 vg of a scAAV9 vector encoding for VEGF under control of the ubiquitous phosphoglycerate kinase promoter (scAAV9-VEGF). An ELISA analysis was performed at 5 months following i.v. injection of the vector to quantify the VEGF protein levels in CNS and non-nervous tissue samples from the scAAV9-VEGF and control non-injected mice. The analysis showed a global increase of the VEGF levels in many tissues of the scAA V9-VEGF-injected mice including the spinal cord. These results suggest an efficient and long-term expression of the VEGF transgene in all mouse tissues including CNS, following systemic scAA V9-mediated VEGF gene transfer in mice.

To our knowledge, these results show, for the first time, that efficient transgene expression can be obtained in cells of the plexus choroids or ependyma, following peripheral administration of a gene transfer vector. These results also represent the first demonstration that recombinant proteins may be secreted into the cerebrospinal fluid upon peripheral administration of a gene transfer vector.

The invention claimed is:

1. A method for expressing a protein in choroid plexus epithelial cells of a human subject, said method comprising:
   intravenously or intra-arterially administering to the human subject an effective amount of a double-stranded self-complementary human serotype 9 adeno-associated virus (AAV9) vector comprising a transgene encoding said protein,
   said administration resulting in said vector crossing the blood-brain barrier and expressing said protein in choroid plexus epithelial cells of said human subject,
   wherein said method is performed in the presence of an intact blood-brain barrier.

2. The method of claim 1, wherein said subject suffers from a disorder of the central nervous system selected from spinal muscular atrophy and amyotrophic lateral sclerosis.

3. The method of claim 1, wherein the AAV vector is a pseudotyped AAV vector.

4. The method of claim 1, wherein the AAV vector comprises a replication defective AAV genome lacking functional Rep and Cap coding viral sequences.

5. The method of claim 1, wherein the protein is selected from the group consisting of growth factors, cytokines, hormones, neurotransmitters, enzymes, anti-apoptotic factors, and angiogenic factors.

6. The method of claim 1, wherein the protein is survival of motor neuron (SMN) protein.

7. The method of claim 1, wherein the vector is a pseudotyped AAV vector comprising an AAV2-derived genome packaged in an AAV9-derived capsid.

8. The method of claim 1, wherein expression of the protein in the vector is controlled by a ubiquitous, regulated or tissue-specific promoter.

9. The method of claim 1, further comprising detecting said protein in the choroid plexus epithelial cells of the human subject.

10. The method of claim 1, wherein said vector is administered by intravenous injection.

11. The method of claim 1, wherein said vector is administered by intraarterial injection.

* * * * *